United States Patent
Shin et al.

(10) Patent No.: US 12,263,206 B2
(45) Date of Patent: Apr. 1, 2025

(54) PHARMACEUTICAL COMPOSITION FOR PREVENTING OR TREATING OBESITY OR SARCOPENIA, CONTAINING IF1 AS ACTIVE INGREDIENT

(71) Applicant: Medi&Gene Inc., Seoul (KR)

(72) Inventors: Min-Jeong Shin, Seoul (KR); Hyeon Soo Kim, Seoul (KR); Ji Hyung Chung, Seoul (KR)

(73) Assignee: Medi&Gene Inc., Seoul (KR)

( * ) Notice: Subject to any disclaimer, the term of this patent is extended or adjusted under 35 U.S.C. 154(b) by 718 days.

(21) Appl. No.: 17/276,212

(22) PCT Filed: Sep. 11, 2019

(86) PCT No.: PCT/KR2019/011865
§ 371 (c)(1),
(2) Date: Mar. 15, 2021

(87) PCT Pub. No.: WO2020/055186
PCT Pub. Date: Mar. 19, 2020

(65) Prior Publication Data
US 2022/0023393 A1    Jan. 27, 2022

(30) Foreign Application Priority Data

Sep. 14, 2018  (KR) .......... 10-2018-0110413
Oct. 2, 2018   (KR) .......... 10-2018-0117692

(51) Int. Cl.
| | | |
|---|---|---|
| *A61K 38/17* | (2006.01) | |
| *A61K 38/00* | (2006.01) | |
| *A61K 38/43* | (2006.01) | |
| *A61P 3/04* | (2006.01) | |
| *A61P 21/00* | (2006.01) | |

(52) U.S. Cl.
CPC ............ *A61K 38/43* (2013.01); *A61K 38/005* (2013.01); *A61P 3/04* (2018.01); *A61P 21/00* (2018.01)

(58) Field of Classification Search
CPC ...... A61K 38/43; A61K 38/005; A61K 38/17; A61P 3/04; A61P 21/00; A23L 33/17
See application file for complete search history.

(56) References Cited

U.S. PATENT DOCUMENTS

| 2004/0072739 A1 | 4/2004 | Anderson et al. |
| 2015/0065556 A1 | 3/2015 | Birsoy et al. |

FOREIGN PATENT DOCUMENTS

| KR | 10-2018-0056628 A | 5/2018 |
| WO | WO 01/34833 A2 | 5/2001 |
| WO | WO 2007/088123 A2 | 8/2007 |

OTHER PUBLICATIONS

Radojkovic et al., Stimulation of Cell Surface F1-ATPase Activity by Apolipoprotein A-I Inhibits Endothelial Cell Apoptosis and Promotes Proliferation, Atheriosclerosis Thrombosis and Vascular Biology, vol. 29, p. 1125-1130. (Year: 2009).*
Arakaki et al., Cell-surface H+-ATP synthase as a potential molecular target for anti-obesity drugs FEBS Letters vol. 581 3405-3409. (Year: 2007).*
Booth, F. W., "Effect of limb immobilization on skeletal muscle," *Journal of applied physiology*, 52, 5, 1982 (pp. 1113-1118).
Mantzoros., Christos S. et al., "Editorial: Leptin as a Therapeutic Agent—Trials and Tribulations", *The Journal of Clinical Endocrinology & Metabolism*, vol. 85, No. 11, 2000 (pp. 1-3).
Roubenoff, Ronenn, et al., "Sarcopenia: Current Concepts." *The Journals of Gerontology Series A: Biological Sciences and Medical Sciences*, 55,12, 2000 (pp. 716-724).
Bodine, Sue C., et al., "Akt/mTOR pathway is a crucial regulator of skeletal muscle hypertrophy and can prevent muscle atrophy in vivo." *Nature cell biology*, 3, 11, 2001 (pp. 1014-1019).
Yoshida, Masasuke, et al., "ATP synthase—a Marvellous rotary engine of the cell." *Nature reviews Molecular cell biology*, 2, 9, 2001 (pp. 669-677).
Emery, Alan EH. "The muscular dystrophies." *The Lancet*, 359, 9307, 2002 (pp. 687-695).
Campanella, Michelangelo, et al., "Regulation of mitochondrial structure and function by the F1Fo-ATPase inhibitor protein, IF1." *Cell metabolism*, 8, 1, 2008 (pp. 13-25).
Genoux, Annelise, et al., "Mitochondrial inhibitory factor 1 (IF1) is present in human serum and is positively correlated with HDL-cholesterol." *PloS one*, 6, 9, 2011 (pp. 1-8).
Heal, David J., et al., "What is the prognosis for new centrally-acting anti-obesity drugs?. " *Neuropharmacology*, 63, 1, 2012 (pp. 132-146).
Heal, D. J. et al.,. "A review of late-stage CNS drug candidates for the treatment of obesity." *International Journal of Obesity*, 37, 1, 2013 (pp. 107-117).
Rodriguez, Julie, et al., "Myostatin and the skeletal muscle atrophy and hypertrophy signaling pathways." Cellular and Molecular Life Sciences 71.22 (2014): 4361-4371.

(Continued)

*Primary Examiner* — Adam Weidner
*Assistant Examiner* — Tiffany M Gough
(74) *Attorney, Agent, or Firm* — NSIP Law

(57) ABSTRACT

The present invention relates to a composition for preventing or treating obesity or sarcopenia, containing ATPase inhibitory factor 1 (IF1) and, more specifically, to a pharmaceutical composition and a food for preventing or treating obesity or sarcopenia, containing, as an active ingredient, IF1 having an effect of suppressed appetite or effects increased muscle mass and muscle production. According to the present invention, ATPase inhibitory factor 1 (IF1) exhibits, in an obesity-induced mouse model, effects of inhibited weight gain and decreased dietary intake without side effects, and exhibits, in obesity-induced or aged mouse, effects of increased muscle mass, increased muscle protein and muscle production, and thus is very useful as an agent for preventing, alleviating or treating metabolic diseases such as obesity, an agent for suppressing appetite and an agent for preventing, alleviating or treating muscle loss-related diseases such as sarcopenia.

9 Claims, 10 Drawing Sheets
Specification includes a Sequence Listing.

(56) References Cited

OTHER PUBLICATIONS

"Mus musculus ATPase inhibitory factor 1 (Atpif1), mRNA", Mus musculus, Feb. 15, 2015 (pp. 1-3).
Formentini, Laura, et al., "Mitochondrial H+-ATP synthase in human skeletal muscle: contribution to dyslipidaemia and insulin resistance," *Diabetologia*, 60, 10, 2017 (pp. 2052-2065).
Kalinkovich, Alexander, et al., "Sarcopenic obesity or obese sarcopenia: a cross talk between age-associated adipose tissue and skeletal muscle inflammation as a main mechanism of the pathogenesis." Ageing research reviews 35 (2017):200-221.
Kahancová, Anežka, et al. "Regulation of glucose-stimulated insulin secretion by ATP ase Inhibitory Factor 1 (IF 1)." FEBS letters 592.6 (2018): 999-1009.
Korean Notice of Allowance issued on Mar. 21, 2021 in counterpart Korean Patent Application No. 10-2019-0110742 (2 pages in Korean).
International Search Report issued on Dec. 24, 2019 in counterpart International Patent Application No. PCT/KR2019/011865 (3 pages in English and 3 pages in Korean).

\* cited by examiner

A

B

PHARMACEUTICAL COMPOSITION FOR PREVENTING OR TREATING OBESITY OR SARCOPENIA, CONTAINING IF1 AS ACTIVE INGREDIENT

CROSS REFERENCE TO RELATED APPLICATIONS

This application is a U.S. National Stage Application of International Application No. PCT/KR2019/011865, filed on Sep. 11, 2019, which claims the benefit under 35 USC 119(a) and 365(b) of Korean Patent Application No. 10-2018-0110413, filed Sep. 14, 2018, and Korean Patent Application No. 10-2018-0117692, filed Oct. 2, 2018 in the Korean Intellectual Property Office, the entire disclosure of which is incorporated herein by reference for all purposes.

TECHNICAL FIELD

The present invention relates to a composition for preventing or treating obesity or sarcopenia containing ATPase inhibitory factor 1 (IF1) and, more specifically, to a pharmaceutical composition and a food for preventing or treating obesity or sarcopenia, containing, as an active ingredient, IF1 having an effect of suppressing appetite or effects of increasing muscle mass and muscle production.

BACKGROUND ART

Obesity is caused by accumulation of excessive energy due to an imbalance in the regulation of accumulation and release of energy, and is considered to be a disease that is more than simply a risk factor for metabolic disorders or diseases in light of the fact that obesity leads to serious diseases, including cardiovascular diseases such as hyperlipidemia, diabetes, arteriosclerosis, and high blood pressure (Mantzoros et al., *J. Clin. Endocrinol. Metab.*, 85:4000-2, 2000).

Efforts to treat obesity are ongoing, and obesity medications and surgical procedures such as liposuction besides exercise therapy and dieting have emerged. There are two main types of current obesity medications: one is a drug that inhibits the absorption of fat or increases the consumption of energy from ingested food, and the other is an "appetite suppressant" that acts on the central nervous system to suppress the appetite. In the former case, although the digestion of ingested food is inhibited or the produced fat is decomposed, when energy is continuously supplied to the body by continuous food ingestion, there is an inevitable limitation. Typical appetite suppressants include Furing® and Pentosin®, containing phendimetrazine, which have the advantages of exerting fast and strong appetite suppressing effect and being inexpensive, but are classified as narcotics and thus continuous administration thereof for one month or more and prescription in combination with other drugs are prohibited. In addition, with regard to Reductil®, Rinovan®, Slimmer®, and the like, which contain sibutramine, voluntary recall recommendations were issued in 2010 in Korea, following the US and Europe, because of the high risk of cardiovascular disease.

Recent rapid development research on obesity drugs has brought about the development of appetite suppressants acting on the central nervous system as novel drugs for treating obesity (D. J. Heal et al., *International Journal of Obesity* 37:107-117, 2013; D. J. Heal et al., *Neuropharmacology* 63:132-146, 2012). As a representative example, in 2012, the US FDA approved two new appetite suppressants, Belviq (lorcaserin) and Qsymia (containing phentermine and topiramate). In addition, exenatide (Byetta) and Liraglutide (Victoza), which are GLP-1 (glucagon-like peptide), are currently approved and marketed as therapeutic agents for type 2 diabetes, and have the effect of suppressing the appetite by increasing satiety. As generally evaluated by Korean medical workers, Belviq is a drug that can be used without concern over side effects, but disadvantageously cannot be expected to realize a remarkable weight loss effect and is expensive, and Qsymia has a weight loss effect superior to that of Belviq, but was not approved for use in Europe due to the high incidence of complications affecting the cardiovascular system and brain, and is not recommended for cardiovascular disease patients.

Therefore, there is an urgent need for novel therapeutic agents for obesity and novel appetite suppressants for obesity treatment that can exhibit remarkable effects while reducing side effects, and the demand therefor is constantly increasing.

In addition, skeletal muscle is an organ that accounts for the largest part of the human body, specifically accounting for 40 to 50% of the total body weight, and plays an important role in various metabolic functions in the body, including energy homeostasis and heat generation. Human muscle mass decreases by more than 1% every year starting at the age of 40, up to 50% of muscle mass is lost by the age of 80, and the loss of muscles in old age is recognized as the most important factor in reducing overall physical function. Such a decrease in muscle strength due to a decrease in skeletal muscle mass during aging is called "sarcopenia".

The aging of the global population is a rapidly spreading social health issue, and the population aging in Korea is rapidly increasing compared to major developed countries. Typical changes in body composition due to aging are an increase in fat mass and a decrease in muscle mass, which means the conversion of muscle to fat, leading to "sarcopenic obesity", which may be considered to fall in a category of obesity which is caused by obesity in combination with sarcopenia. In particular, obesity and sarcopenia, which occur concurrently in the elderly population, may act as a risk factor for metabolic diseases and increase the risk of death (Kalinkovich A. et al., *Aging. Res. Rev.* 35:200-221, 2017).

Sarcopenia is caused by a variety of factors, but research on individual factors is still insufficient. Sarcopenia is caused by decreased growth hormone levels, neurological changes, changes in physiological activity, changes in metabolism, increases in the amount of sex hormones, or increases in fat or catabolic cytokines, and changes in the balance between protein synthesis and differentiation (Roubenoff R. and Hughes V. A., *J. Gerontol. A. Biol. Sci. Med. Sci.* 55: M716-M724, 2000).

Muscular atrophy is caused by factors such as damage to muscle tissue due to the absence of mechanical stimulation such as decreased use of muscles, destruction of muscle due to direct injury or physical factors, impairment of the resilience of muscle cells due to aging, and impairment of muscle use due to damage to nerves that control muscle action (Booth F. W. et al., *J. Appl. Physiol. Respir. Environ. Exerc. Physiol.*, 1982). A general type of muscular atrophy is disuse atrophy, which is gradually induced by loss of muscle strength due to long-term disuse of muscles in an area damaged by a disorder or accident and the surrounding area thereof. Other examples of muscular atrophy include myasthenia gravis and muscular dystrophy caused by muscle diseases, and spinal muscular amyotrophy, amyotrophic lateral sclerosis (ALS), and spinobulbar muscular atrophy, caused by inflammation that occurs in the muscles and damage to the nerves that control the muscles, and the like.

Various studies are conducted on methods to effectively control sarcopenia, and a method of inhibiting muscular atrophy caused by degeneration or progressive variation of muscle cells, which is a type of sarcopenia, is used as a method of slowing the progression of sarcopenia. For example, WO 2007/088123 discloses a therapeutic agent for muscular dystrophy containing a nitroxy derivative as an active ingredient, and WO 2006/081997 discloses a therapeutic agent for muscular atrophy containing atraric acid or a derivative thereof as an active ingredient. However, these therapeutic agents containing the compounds as active ingredients act not only on skeletal muscles in which muscular dystrophy has occurred, but also on visceral muscles or the myocardium, which are not related to muscular dystrophy, and thus are not used in practice for treatment due to the possibility of causing various side effects. In addition, treatment with growth hormone (GH) has been found to increase muscle mass, but is disadvantageously very expensive.

Therefore, there is an urgent need to develop drugs and methods effective for sarcopenia treatment that can delay the progression of sarcopenia even in elderly patients or bed-ridden patients, without causing side effects.

Meanwhile, energy generation in cells constituting the human body is one of the most essential elements for survival, and mitochondria present in cells are important organs involved in metabolism through such energy generation and regulation. Mitochondria form an electron transport system in the inner mitochondrial membrane (IMM) of the double cell membrane composed of the outer mitochondrial membrane and the inner mitochondrial membrane to induce oxidative phosphorylation. ATPase, which is the fifth of the five structures that constitute the electron transport system, contributes to the synthesis of ATP, and is emphasized in importance because ATP is the most effective in energy transfer and substance activation and is a substance that is used in an amount of about 40 kg per day in an adult human body (Yoshida et al., *Nat. Rev. Mol. Cell. Biol.* 2(9):669-77, 2001).

ATPase inhibitory factor 1 (IF1) binds to F1Fo ATP synthase (multi-subunit, membrane-bound assembly), which is involved in the synthesis and degradation of ATP in the mitochondria; that is, IF1 binds to β-F1-ATPase in the cell membrane to thereby induce intracellular signaling systems such as the PI3K-Akt pathway and cause a biological response based thereon.

However, all conventional studies associated with IF1 focus on only evaluation of the functions of endogenous IF1, and do not report efficacy of exogenous IF1 in the treatment of obesity or the mechanism thereof.

In addition, the present inventors have found that when L6 myoblasts are treated with IF1, the ATP concentration in the medium is significantly increased, and phosphorylation of Akt in muscle cells is improved by the cell-signaling system triggered at that time. Recent studies have reported that Akt phosphorylation in muscle cells and the subsequent mTORC pathway activation delay protein degradation and promote protein synthesis (Bodine et al., *Nat. Cell Biol.* 3(11):1014-9, 2001). In addition, it is known that an increase in the expression level of myostatin, which is known as a negative regulator for muscle growth, causes muscular atrophy and sarcopenia by regulating the expression level of myogenic marker genes (Rodriguez et al., *Cell. Mol. Life Sci.* 71(22): 4361-71, 2014). Therefore, it can be seen that IF1 induces an increase in the extracellular ATP concentration through the interaction with the F1-ATPase subunit of the muscle cell membrane, and this is the basis for inferring that muscle production can be promoted and muscular atrophy and sarcopenia can be inhibited through the subsequent metabolic signaling.

In response thereto, as a result of extensive efforts to develop therapeutic agents for obesity and sarcopenia that exhibit excellent effects without causing side effects, the present inventors found that administration of IF1 recombinant proteins suppressed weight gain, decreased dietary intake in obesity-induced mice, and increased muscle mass and muscular protein mass in obese mice or aged mice. Based on this finding, the present invention has been completed.

DISCLOSURE

Technical Problem

Therefore, the present invention has been made in view of the above problems, and it is one object of the present invention to provide a pharmaceutical composition and a food for preventing or treating obesity containing, as an active ingredient, ATPase inhibitory factor 1 (IF1) having effects of reducing weight and suppressing appetite.

It is another object of the present invention to provide a pharmaceutical composition and a food for preventing or treating sarcopenia, containing, as an active ingredient, ATPase inhibitory factor 1 (IF1) having effects of increasing muscular mass and muscle production.

Technical Solution

In accordance with one aspect of the present invention, the above and other objects can be accomplished by the provision of a pharmaceutical composition for preventing or treating obesity comprising IF1 (ATPase inhibitory factor 1) as an active ingredient.

In accordance with another aspect of the present invention, provided is a food for preventing or alleviating obesity comprising IF1 (ATPase inhibitory factor 1) as an active ingredient.

In accordance with another aspect of the present invention, provided is a method for preventing or treating obesity comprising administering IF1 (ATPase inhibitory factor 1) to a subject.

In accordance with another aspect of the present invention, provided is the use of IF1 (ATPase inhibitory factor 1) for the prevention or treatment of obesity.

In accordance with another aspect of the present invention, provided is the use of a pharmaceutical composition comprising IF1 (ATPase inhibitory factor 1) as an active ingredient for the prevention or treatment of obesity.

In accordance with another aspect of the present invention, provided is the use of IF1 (ATPase inhibitory factor 1) for the preparation of a drug for the prevention or treatment of obesity.

In accordance with another aspect of the present invention, provided is a pharmaceutical composition for suppressing appetite comprising IF1 (ATPase inhibitory factor 1) as an active ingredient.

In accordance with another aspect of the present invention, provided is a functional food for suppressing appetite comprising IF1 (ATPase inhibitory factor 1) as an active ingredient.

In accordance with another aspect of the present invention, provided is a method of suppressing appetite comprising administering IF1 (ATPase inhibitory factor 1) to a subject.

In accordance with another aspect of the present invention, provided is the use of IF1 (ATPase inhibitory factor 1) for appetite suppression.

In accordance with another aspect of the present invention, provided is the use of a pharmaceutical composition comprising IF1 (ATPase inhibitory factor 1) as an active ingredient for appetite suppression.

In accordance with another aspect of the present invention, provided is the use of IF1 (ATPase inhibitory factor 1) for the preparation of a drug for suppressing appetite.

In accordance with another aspect of the present invention, provided is a pharmaceutical composition for preventing or treating sarcopenia comprising IF1 (ATPase inhibitory factor 1) as an active ingredient.

In accordance with another aspect of the present invention, provided is a food for preventing or alleviating sarcopenia comprising IF1 (ATPase inhibitory factor 1) as an active ingredient.

In accordance with another aspect of the present invention, provided is a method for preventing or treating sarcopenia comprising administering IF1 (ATPase inhibitory factor 1) to a subject.

In accordance with another aspect of the present invention, provided is the use of IF1 (ATPase inhibitory factor 1) for the prevention or treatment of sarcopenia.

In accordance with another aspect of the present invention, provided is the use of a pharmaceutical composition comprising IF1 (ATPase inhibitory factor 1) as an active ingredient for the prevention or treatment of sarcopenia.

In accordance with another aspect of the present invention, provided is the use of IF1 (ATPase inhibitory factor 1) for the preparation of a drug for preventing or treating sarcopenia.

BEST MODE

Figure 1:
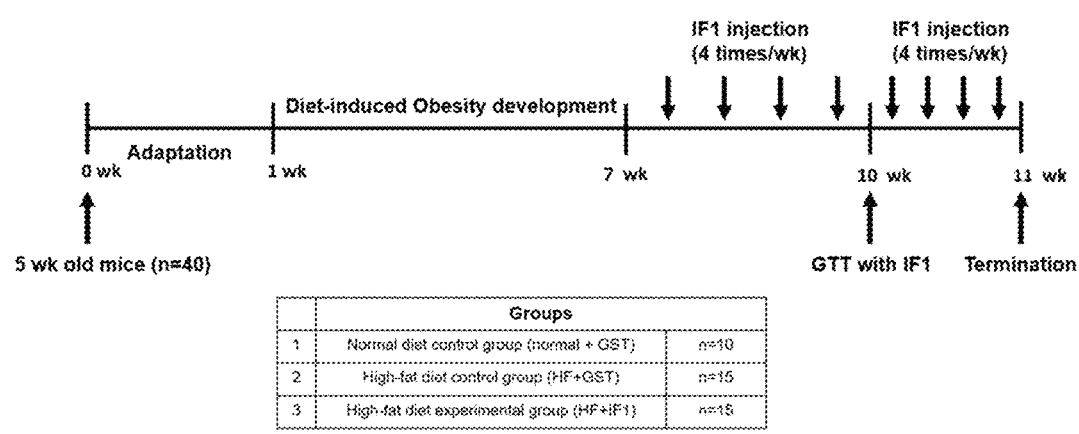
FIG. 1 shows the overall experimental schedule regarding obesity induction and IF1 administration in mice.

Unless defined otherwise, all technical and scientific terms used herein have the same meanings as appreciated by those skilled in the field to which the present invention pertains. In general, the nomenclature used herein is well-known in the art and is ordinarily used.

ATPase inhibitory factor 1 (hereinafter, referred to as IF1) is a 9.6-kDa basic protein composed of 84 amino acids, and is encoded by the ATP5IF1 gene. ATPase consists of F0 and F1 domains, and central and peripheral stalks, and is subdivided into several subunits. IF1 has been actively researched as a major protein that interferes with the function of ATPase, and is a target that is naturally produced in the human body and regulates ATP production and degradation by the mitochondria (Campanella et al., *Cell Metab.*, 8:13-25, 2008). The inhibitory activity of IF1 is initiated by binding to the α and β subunit sites of ATPase to interfere with rotational motion. IF1 binds to the F1-ATPase subunit located in the plasma membrane, and at this time, ATP hydrolysis is inhibited through the regulation of F1-ATPase activity, causing an increase in extracellular ATP (exATP). exATP reacts with the purine receptor of the plasma membrane and then triggers a variety of useful intracellular responses through purine signaling.

However, the mechanisms for controlling obesity and the mechanisms associated with muscle mass increase, muscle protein increase, or myogenesis of IF1 are not known at all.

Therefore, in the present invention, based on the whole mouse IF1 mRNA sequence (NCBI No. NM_007512.3), the DNA data of IF1 including GST-tag was cloned to produce a recombinant protein (SEQ ID NO: 1), and the recombinant IF1 was administered to an obesity-induced mouse model to detect the effects of IF1 on suppression of weight gain, reduction of dietary intake, reduction of total visceral fat mass and reduction of liver weight. In addition, recombinant IF1 was administered to obese mouse and aged mouse models to detect the effects of IF1 on increases in muscle mass, muscular protein mass, myogenesis, and the like. That is, the anti-obesity effect and prophylactic and therapeutic effects for sarcopenia of ATPase inhibitory factor 1 (IF1) were demonstrated.

Therefore, in one aspect, the present invention is directed to a pharmaceutical composition for preventing or treating obesity comprising IF1 (ATPase inhibitory factor 1) as an active ingredient.

In the present invention, the obesity comprises complications due to obesity.

The complications due to obesity include one or more selected from the group consisting of visceral fat syndrome, metabolic abnormality syndrome, hypertriglyceridemia, hypo-high-density lipoproteinemia, angina pectoris, myocardial infarction, osteoarthritis, weight-gain-related cancer, orthostatic hypotension, pulmonary hypertension, diabetes, hypertension, impaired glucose tolerance, coronary artery thrombosis, atherosclerosis, gallbladder diseases such as cholelithiasis, insulin resistance, chronic arterial obstruction, thromboembolism, heart disease, lipid syndrome, and hyperglycemia, but are not limited thereto.

As used herein, the term "obesity" refers to a condition or disease characterized by excess body fat due to energy imbalance. Obesity can be prevented or treated through weight loss by administering the pharmaceutical composition according to the present invention to a subject.

As used herein, the term "prevention" refers to any action that can suppress or delay the onset of obesity by administration of the pharmaceutical composition according to the present invention.

As used herein, the term "treatment" refers to any action that can ameliorate or beneficially alter the symptoms of obesity by administration of the pharmaceutical composition according to the present invention.

The obesity treatment can be applied to any mammal in which obesity may occur, and examples thereof include, without limitation, livestock such as cattle, pigs, sheep, horses, dogs and cats, as well as humans and primates, but preferably humans.

As used herein, the term "administration" refers to an action of introducing a predetermined substance into a subject by any appropriate method, and the route of administration of the compositions may be any general route, so long as it enables the drug to be delivered to target tissue. The route of administration may include, but is not limited to, intraperitoneal administration, intravenous administration, intramuscular administration, subcutaneous administration, intradermal administration, oral administration, topical administration, intranasal administration, intrapulmonary administration, rectal administration and the like.

In addition, in the present invention, it was specifically confirmed through a change in norepinephrine (NE) that IF1 regulates diet and energy metabolism through activation of the nervous system.

Norepinephrine (NE) is known as a major neurotransmitter in the sympathetic nervous system, and is known to suppress appetite through activation of the central nervous system.

ATPase inhibitory factor 1 (IF1) of the present invention increases norepinephrine and increases the expression level of the UCP-1 gene, which regulates energy metabolism by conversion of white fat to brown fat.

Therefore, in another aspect, the present invention is directed to a pharmaceutical composition for suppressing appetite containing IF1 (ATPase inhibitory factor 1) as an active ingredient.

As used herein, the term "appetite suppression" refers to any action that suppresses or delays appetite by administration of the composition.

The pharmaceutical composition of the present invention may be administered in a pharmaceutically effective amount, and the term "pharmaceutically effective amount" refers to an amount which is sufficient for treating or preventing a disease at a reasonable benefit/risk ratio applicable to medical treatment or prevention, and the effective dosage level may be determined depending on a variety of factors including severity of the disease, activity of the drug, the age, body weight, health condition and gender of the patient, sensitivity of the patient to the drug, administration time, administration route and excretion rate of the composition according to the present invention, treatment period, and drugs mixed with the used composition of the present invention or used concurrently therewith, and other factors well-known in the pharmaceutical field.

The pharmaceutical composition of the present invention may be administered as a single therapeutic agent or in combination with other therapeutic agents, and may be administered sequentially or simultaneously with a conventional therapeutic agent. In addition, the pharmaceutical composition may be administered single or multiple. Taking into consideration these factors, it is important to administer the minimum amount sufficient to achieve maximum efficacy without side effects.

In addition, the dosage (administered amount) of the pharmaceutical composition according to the present invention may be determined by those skilled in the art in consideration of the purpose of use, the severity of the disease, the patient's age, weight, gender and history, the type of substances used as active ingredients, and the like. For example, the pharmaceutical composition of the present invention may be administered to an adult in a daily dose of 10 mg/kg to 100 mg/kg, more preferably 10 mg/kg to 30 mg/kg. The composition of the present invention may be administered one to three times a day, or may be administered several times after being divided into multiple doses, but the frequency of administration of the composition is not particularly limited thereto.

The pharmaceutical composition of the present invention may be prepared in the form of a pharmaceutical composition for treating or preventing obesity, further containing an appropriate carrier, excipient or diluent commonly used in the preparation of pharmaceutical compositions, and the carrier may include a non-naturally-occurring carrier.

Specifically, the pharmaceutical composition may be formulated and used as an oral formulation such as a powder, granule, tablet, capsule, suspension, emulsion, syrup, or aerosol, or an external preparation, suppository or sterile injectable solution.

Examples of the carrier, excipient and diluent that may contained in the pharmaceutical composition according to the present invention may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. Upon preparation of a formulation, typically used diluents or excipients, such as fillers, extenders, binders, wetting agents, disintegrants or surfactants are used.

Solid formulations for oral administration may include, but are not limited to, tablets, pills, powders, granules, capsules and the like, and these solid formulations may be prepared by mixing at least one excipient, for example, starch, calcium carbonate, sucrose, lactose, gelatin, or the like. In addition to simple excipients, lubricants such as magnesium stearate and talc are also used.

Liquid formulations for oral administration may be suspensions, oral liquids and solutions, emulsions, syrups and the like, and may include various excipients such as wetting agents, sweeteners, fragrances, preservatives and the like, in addition to water and liquid paraffin, which are simple diluents that are commonly used. Formulations for parenteral administration may include sterilized aqueous solutions, non-aqueous solvents, suspensions, emulsions, freeze-dried preparations and suppositories. Examples of such non-aqueous solvents and suspensions include propylene glycol, polyethylene glycol, vegetable oil such as olive oil, injectable esters such as ethyl oleate, and the like.

The pharmaceutical composition of the present invention may be a sterile injectable formulation such as a sterile injectable aqueous or oily suspension. This suspension may be formulated according to techniques known in the art using suitable dispersing or wetting agents (e.g. Tween 80) and suspending agents. The sterile injectable formulation may also be a sterile injectable solution or suspension in a non-toxic parenterally acceptable diluent or solvent (e.g., a solution in 1,3-butanediol). Pharmaceutically acceptable vehicles and solvents include mannitol, water, Ringer's solution and isotonic sodium chloride solution. In addition, sterile nonvolatile oils are commonly used as solvents or suspension media. For this purpose, any less irritating non-volatile oil including synthetic mono- or diglycerides may be used. Fatty acids such as oleic acid and glyceride derivatives thereof, like pharmaceutically acceptable natural oils (e.g. olive oil or castor oil), particularly polyoxyethylated natural oils thereof, are useful for injectable formulations.

The pharmaceutical composition of the present invention may also be administered in the form of a suppository for rectal administration. The composition can be prepared by mixing a compound of the present invention with a suitable non-irritating excipient which is solid at room temperature but liquid at rectal temperature. Such a substance includes, but is not limited to, cocoa butter, beeswax and polyethylene glycol.

Parenteral administration of the pharmaceutical composition according to the present invention is particularly useful when the desired treatment relates to an easily accessible area or organ by topical application. When the pharmaceutical composition of the present invention is applied topically to the skin, the pharmaceutical composition should be formulated as a suitable ointment containing the active ingredient suspended or dissolved in a carrier. Carriers for topical administration of the compound of the present invention include, but are not limited to, mineral oil, liquid paraffin, white vaseline, propylene glycol, polyoxyethylene, polyoxypropylene compounds, emulsifying wax and water. Alternatively, the pharmaceutical composition may be formulated as a suitable lotion or cream containing the active compound suspended or dissolved in a carrier. Suitable carriers include, but are not limited to, mineral oil, sorbitan monostearate, polysorbate 60, cetyl ester wax, cetearyl alcohol, 2-octyldodecanol, benzyl alcohol and water. The pharmaceutical composition of the present invention can also be applied topically to the lower intestine as a rectal suppository or a suitable enema. Topically applied transdermal patches also fall within the scope of the present invention.

The pharmaceutical composition of the present invention can be administered by nasal aerosol or inhalation. The composition can be prepared as a solution in saline using benzyl alcohol or other suitable preservatives, absorption accelerators to enhance bioavailability, fluorocarbons, and/or other solubilizing or dispersing agents known in the art according to techniques well known in the field of pharmaceuticals.

The content of the drug contained in the pharmaceutical composition of the present invention in is 0.0001 to 50% by weight, and more preferably 0.01 to 10% by weight, based on the total weight of the final composition, but is not particularly limited thereto.

In another aspect, the present invention is directed to a method for preventing or treating obesity comprising administering a pharmaceutical composition containing IF1 (ATPase inhibitory factor 1) as an active ingredient to a subject.

In another aspect, the present invention is directed to the use of IF1 (ATPase inhibitory factor 1) for the prevention or treatment of obesity.

In another aspect, the present invention is directed to the use of a pharmaceutical composition comprising IF1 (ATPase inhibitory factor 1) as an active ingredient for the prevention or treatment of obesity.

In another aspect, the present invention is directed to the use of IF1 (ATPase inhibitory factor 1) for the preparation of a drug for the prevention or treatment of obesity.

In another aspect, the present invention is directed to a method of suppressing appetite comprising administering a pharmaceutical composition comprising IF1 (ATPase inhibitory factor 1) as an active ingredient to a subject.

In another aspect, the present invention is directed to the use of IF1 (ATPase inhibitory factor 1) for appetite suppression.

In another aspect, the present invention is directed to the use of a pharmaceutical composition comprising IF1 (ATPase inhibitory factor 1) as an active ingredient for appetite suppression.

In another aspect, the present invention is directed to the use of IF1 (ATPase inhibitory factor 1) for the preparation of an appetite suppressant.

As used herein, the term "subject" refers to any animal, including a human, that suffers from or is at risk of obesity, and the disease can be effectively prevented or treated by administering the composition according to the present invention thereto.

In another aspect, the present invention is directed to a food for preventing or alleviating obesity comprising IF1 (ATPase inhibitory factor 1) as an active ingredient.

In the present invention, the obesity may include complications due to obesity.

The complications due to obesity may include one or more selected from the group consisting of visceral fat syndrome, metabolic abnormality syndrome, hypertriglyceridemia, hypo-high-density lipoproteinemia, angina pectoris, myocardial infarction, osteoarthritis, weight-gain-related cancer, orthostatic hypotension, pulmonary hypertension, diabetes, hypertension, impaired glucose tolerance, coronary artery thrombosis, atherosclerosis, gallbladder diseases such as cholelithiasis, insulin resistance, chronic arterial obstruction, thromboembolism, heart disease, lipid syndrome and hyperglycemia, but are not limited thereto.

As used herein, the term "amelioration" refers to any action that at least reduces the severity of the parameters associated with the condition to be treated, e.g. the degree of symptoms.

In another aspect, the present invention is directed to a functional food for suppressing appetite comprising IF1 (ATPase inhibitory factor 1) as an active ingredient.

When the food composition of the present invention is used as a food additive, the food composition may be used alone or in combination with other food or food additives, and can be suitably used in accordance with a conventional method. In general, when preparing food or a beverage, the composition of the present invention is added in an amount of 15% by weight or less, preferably 10% by weight or less, based on the raw material. However, in the case of long-term intake for the purpose of health and hygiene or for the purpose of health management, the amount may be within the range defined above, and it will be obvious that the active ingredient may be used in an amount exceeding the above range because there is no problem in terms of safety.

The food of the present invention may be prepared in any form such as a functional food, nutritional supplement, health food or food additive. For example, the composition of the present invention as a health food may be prepared in the form of a tea, juice or drink for drinking, or may be granulated, encapsulated and powdered for ingestion. In addition, functional foods may be prepared by adding the composition of the present invention to beverages (including alcoholic beverages), fruits and processed foods thereof (e.g., canned fruit, bottled fruit, jam, marmalade, etc.), fish, meat and processed foods thereof (e.g., ham, sausage, corned beef, etc.), bread and noodles (e.g. udong, soba, ramen, spaghetti, macaroni, etc.), fruit juice, various drinks, cookies, Yeot (Korean hard taffy), dairy products (e.g. butter, cheese, etc.), edible vegetable oils, margarine, vegetable protein, food contained in a retort pouch, frozen food, various seasonings (e.g., miso, soy sauce, sauce, etc.), and the like.

The health functional food includes, as a food composition, various forms such as functional foods, nutritional supplements, health foods, food additives, etc., and the health functional food may be provided by preparing the composition of the present invention in various forms, such as teas, juices or drinks, or performing granulation, encapsulation, or powderization, or by adding these compounds or extracts to various foods such as beverages, fruits and processed foods, fish, meat and processed foods, breads, noodles, seasonings and the like according to conventional methods known in the art.

The health beverage composition may contain additional ingredients such as various flavors or natural carbohydrates, like general beverages. The natural carbohydrates include monosaccharides such as glucose and fructose, disaccharides such as maltose and sucrose, natural sweeteners such as dextrin and cyclodextrin. In addition, synthetic sweeteners such as saccharin and aspartame may be used. The proportion of the natural carbohydrate can be appropriately selected by those skilled in the art.

In addition to the ingredients described above, the composition of the present invention may contain various nutrients, vitamins, electrolytes, flavoring agents, colorants, pectic acids and salts thereof, alginic acid and salts thereof, organic acids, protective colloidal thickeners, pH adjusters, stabilizers, preservatives, glycerin, alcohols, carbonating agents used in carbonated beverages, and the like. In addition, the composition of the present invention may contain pulp for the production of natural fruit juices, fruit juice beverages and vegetable beverages. These components may be used alone or in combination. The proportion of these additives can also be appropriately selected by those skilled in the art.

In another aspect, the present invention is directed to a pharmaceutical composition for preventing or treating sarcopenia comprising IF1 (ATPase inhibitory factor 1) as an active ingredient.

In the present invention, the composition may increase muscle mass or prevent muscle loss.

In the present invention, the sarcopenia may be caused by aging or obesity.

As used herein, the term "muscular reduction due to aging" refers to a gradual decrease in skeletal muscle mass or a gradual reduction in muscle density and function according to aging, and refers to a condition that directly causes a decrease in muscle strength, and as a result, can cause reduction and loss of various bodily functions.

The muscle-aging-related disease may include, but is not limited to, age-related sarcopenia, motion neuron disease, metabolic muscle disease, inflammatory myopathy, neuromuscular junction disease, and endocrine myopathy.

In the present invention, the sarcopenia is preferably selected from the group consisting of muscular atrophy, disuse atrophy, spinal muscular amyotrophy, dystrophy, spasticity, muscular hypotonia, muscle weakness, muscular dystrophy, amyotrophic lateral sclerosis, spinobulbar muscular atrophy, and myasthenia gravis, but is not limited thereto.

As used herein, the term "sarcopenia" refers to a disease characterized by reduced muscle mass and specifically refers to a disease characterized by gradual reduction of muscle volume and muscle strength. In particular, it refers to a disease in which the muscles of the limbs gradually atrophy substantially bilateral symmetrically, and may accompany cancer, aging, kidney diseases, inherited diseases, various chronic diseases, spinal muscular atrophy, and the like. Sarcopenia includes muscular atrophy characterized in that the muscles atrophy and representative examples thereof include amyotrophic lateral sclerosis (Lou Gehrig's disease) and spinal muscular atrophy.

As used herein, the term "muscular atrophy" is preferably muscular atrophy due to loss of muscle tissue caused by disuse of muscles, muscular atrophy due to disease of the muscle itself, or muscular atrophy due to damage to nerves that control the muscles. The muscular atrophy due to loss of muscle tissue caused by disuse of the muscles is more preferably disuse atrophy, the muscular atrophy due to disease of the muscle itself is more preferably myasthenia gravis or dystrophy such as progressive muscular dystrophy, myotonic muscular dystrophy, Duchenne muscular dystrophy, Becker muscular dystrophy, limb-girdle muscular dystrophy, or facioscapulohumeral muscular dystrophy, and the muscular atrophy due to inflammation of the muscle itself and muscular atrophy due to damage to the nerves that control muscles more preferably include spinal muscular amyotrophy such as Werdnig-Hoffmann disease and Kugelberg Welander syndrome, amyotrophic lateral sclerosis, also known as Lou Gehrig's disease, and spinobulbar muscular atrophy, also known as Kennedys disease, but are not limited thereto.

The disease related to muscle aging, including age-related sarcopenia, is distinguished from muscular dystrophy or muscular atrophy.

Specifically, muscular dystrophy patients exhibit muscle necrosis upon muscle biopsy, have uneven and various muscle fiber sizes, and exhibit symptoms in which fat and fibrotic tissue are replaced at the necrosis sites of muscle fibers. Typically known muscular dystrophy includes Becker muscular dystrophy, Duchenne muscular dystrophy, congenital muscular dystrophy and Emery-Dreifuss muscular dystrophy (Alan E H Emery, Lancet 23; 359(9307):687-95, 2002).

In addition, muscular atrophy means atrophy of the muscles of the limbs, includes amyotrophic lateral sclerosis and spinal muscular atrophy as representative examples thereof, and is known to be a disease caused by progressive degeneration of motor nerve fibers and cells in the spinal cord.

Specifically, the spinal muscular amyotrophy is a genetic disorder caused by degeneration of motor neurons of the spinal cord, and is known to be a neuromuscular disease afflicting infants and children. In addition, amyotrophic lateral sclerosis is characterized by intractable and irreversible neurodegenerative changes due to the death of upper and lower motor neurons in the cerebrum and spinal cord, and the major factors thereof are known to be lack of neuronal growth factors and neuroinflammation.

Currently, methods of treating sarcopenia due to aging include the use of urocortin II, hormone replacement therapy and the like. However, these methods are insufficient for the fundamental treatment for diseases related to muscle aging, because some side effects thereof have been reported.

According to a specific embodiment of the present invention, it was found that administration of IF1 of the present invention to mice increased muscle mass and muscle protein mass and also affected the expression of genes related to muscle production and degradation. This showed that IF1 effectively restores and improves muscle functions by increasing muscle mass and preventing muscle loss.

The therapeutic effect of IF1 can be equally applied to muscular atrophy as well as sarcopenia caused by various factors such as cancer and aging.

As used herein, the term "prevention" refers to any action that can suppress or delay the onset of sarcopenia or muscle use-related disorders by administration of the pharmaceutical composition according to the present invention.

As used herein, the term "treatment" refers to any action that can ameliorate or beneficially alter the symptoms of sarcopenia or muscle use-related disorders by administration of the pharmaceutical composition according to the present invention.

The sarcopenia treatment can be applied to any mammal in which sarcopenia or muscle use-related disorders may occur, and examples thereof include, without limitation, livestock such as cattle, pigs, sheep, horses, dogs and cats, as well as humans and primates, but preferably humans.

In another aspect, the present invention is directed to a method for preventing or treating sarcopenia comprising administering a pharmaceutical composition comprising IF1 (ATPase inhibitory factor 1) as an active ingredient to a subject.

In another aspect, the present invention is directed to the use of IF1 (ATPase inhibitory factor 1) for the prevention or treatment of sarcopenia.

In another aspect, the present invention is directed to the use of a pharmaceutical composition comprising IF1 (ATPase inhibitory factor 1) as an active ingredient for the prevention or treatment of sarcopenia.

In another aspect, the present invention is directed to the use of IF1 (ATPase inhibitory factor 1) for the preparation of a drug for preventing or treating sarcopenia.

As used herein, the term "subject" refers to any animal, including a human, that suffers from or is at risk of sarcopenia, and the disease can be effectively prevented or treated by administering the composition according to the present invention thereto.

In another aspect, the present invention is directed to a food for preventing or alleviating sarcopenia comprising IF1 (ATPase inhibitory factor 1) as an active ingredient.

As used herein, the term "amelioration" refers to any action that at least reduces the severity of the parameters associated with the condition to be treated, e.g. the degree of symptoms.

In the present invention, the food may increase muscle mass or prevent muscle loss.

In the present invention, the sarcopenia may be caused by aging or obesity.

In the present invention, the sarcopenia is preferably selected from the group consisting of muscular atrophy, disuse atrophy, spinal muscular amyotrophy, dystrophy, spasticity, muscular hypotonia, muscle weakness, muscular dystrophy, amyotrophic lateral sclerosis, spinobulbar muscular atrophy, and myasthenia gravis, but is not limited thereto.

EXAMPLE

Hereinafter, the present invention will be described in more detail with reference to examples. However, it will be obvious to those skilled in the art that these examples are provided only for illustration of the present invention and should not be construed as limiting the scope of the present invention.

Example 1: Production of Obesity-Induced Animal Model

C57BL/6J male mice were used as animal models, and 5-week-old mice were obtained from JOONGAH BIO, fed a regular diet for 1 week and acclimated for an adaptation period. The mice were bred under a constant environment including a humidity of 50 to 60% and a temperature of 18 to 24° C., and were freely fed during both the adaptation period and the experiment period.

After the 1-week adaptation period, the mice were classified into 3 groups and reared for 6 weeks under the following conditions.

Group 1: Normal diet (ND) control group (n=10)
Group 2: High-fat diet (HFD) control group (n=15)
Group 3: High-fat diet (HFD) experimental group (n=15)

The normal diet and the high-fat diet were prepared and provided as shown in Table 1 below.

TABLE 1

Ingredients of normal diet (ND) and high-fat diet (HFD; 40%)

| Ingredients | ND (g) | HFD (g) |
|---|---|---|
| Corn starch | 15 | 15 |
| Casein | 20 | 20 |

TABLE 1-continued

Ingredients of normal diet (ND) and high-fat diet (HFD; 40%)

| Ingredients | ND (g) | HFD (g) |
|---|---|---|
| Sucrose | 50 | 34 |
| corn oil | 5 | 3 |
| Mineral mix | 3.5 | 3.5 |
| Vitamin mix | 1 | 1 |
| Cellulose | 5 | 5 |
| DL-methionine | 0.3 | 0.3 |
| Choline bitartrate | 0.2 | 0.2 |
| Lard | | 17 |
| Cholesterol | | 1 |
| BHT | 0.001 | 0.001 |
| Total | 100 (g) | 100 (g) |

After completion of the 1-week adaptation period, obesity was induced in the mice for 6 weeks using the high-fat diet, and then the mice were administered with IF1. The overall experimental schedule including obesity induction and IF1 administration in mice is shown in FIG. 1.

Example 2: Effect of IF1 Administration on Weight Gain Inhibition

IF1 (5 mg/kg BW) was intraperitoneally injected 4 times a week for 4 weeks into the mice that had been constantly subjected to obesity induction for 6 weeks after the adaptation period of one week (FIG. 1). For IF1, DNA data of IF1 including GST-tag were isolated and purified through cloning to produce a recombinant protein.

The conditions for administering IF1 to the three mouse groups of Example 1 were as follows.

Group 1: Normal diet (ND) control group+GST intraperitoneal injection (n=10)

Group 2: High-fat diet (HFD) control group+GST intraperitoneal injection (n=15)

Group 3: High-fat diet (HFD) experimental group+IF1 intraperitoneal injection (n=15) (5 mg/kg BW)

While IF1 was administered to the obesity-induced mice for 4 weeks, body weight was measured immediately before administration of IF1 on the day of intraperitoneal injection.

Figure 2:
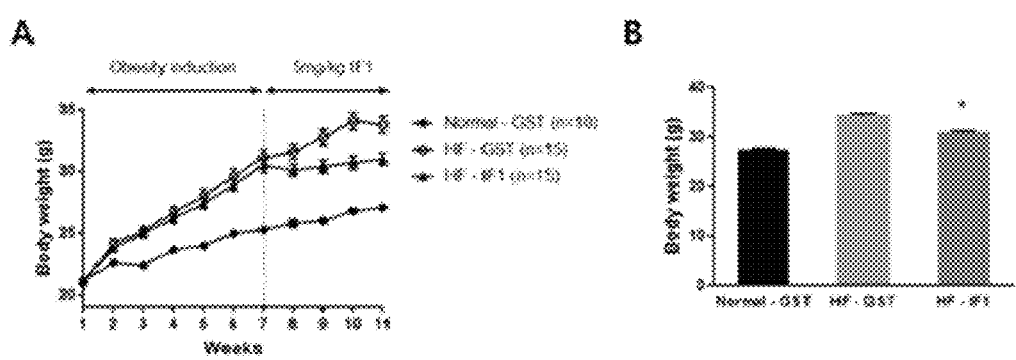
FIG. 2 shows the effect of weight reduction in mice due to treatment with IF1, wherein (A) shows the weight change over time, (B) shows the final weight after 4 weeks of IF1 administration, and *P<0.05 is satisfied upon comparison with an HF-GST group.

As a result, the IF1-administered group exhibited significantly suppressed weight gain compared to the high-fat-diet control group from 7 weeks after IF1 administration (FIG. 2A). That is, the body weight increased rapidly until 7 weeks after induction of obesity with the high-fat diet, but the weight gain was suppressed during the 4 weeks of IF1 administration following the 7 weeks. FIG. 2B shows a comparison of the final mouse weight between the groups at the end of the 11$^{th}$ week.

Example 3: Reduction of Dietary Intake Due to IF1 Administration

Feed intake was measured daily for 4 weeks of IF1 administration to 3 mouse groups.

Figure 3:
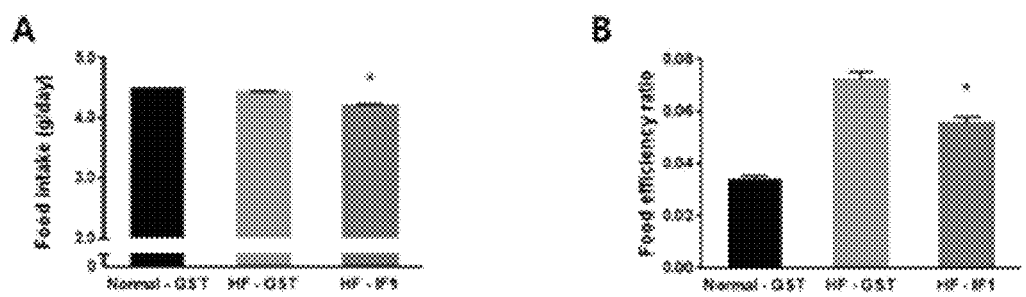
FIG. 3 shows the change in dietary intake in mice due to treatment with IF1, wherein (A) shows the value obtained by dividing the total dietary intake (g) by the day of the experiment, and (B) shows FER (food efficiency ratio), wherein FER is calculated as a weight gain (g/day)/dietary intake (g/day) and *P<0.05 is satisfied upon comparison with an HF-GST group.

FIG. 3A shows the difference in dietary intake (the total dietary intake g/day) between the three groups. As a result, the IF1-administered group exhibited a statistically significant decrease in dietary intake compared to the high-fat-diet group.

Then, FER (food efficiency ratio, FER=weight gain/dietary intake) was calculated by dividing the weight gained by the mouse (g/day) by the dietary intake (g/day). As a result, the IF1-administered group was found to exhibit a decrease in FER compared to the high-fat-diet group (FIG. 3B). The result showed that the effect of suppressing weight gain in obese mice was due to the decrease in dietary intake due to appetite suppression.

Example 4: Reduced Fat Accumulation in Tissue and Increased Muscle Mass Due to IF1 Administration The mice were dissected and tissue was obtained therefrom after 11 weeks at which all experiments were completed containing 4 weeks of IF1 administration. For dissection, the mice were fasted for 16 hours, and the next day, the mice were completely anesthetized by intraperitoneal injection of 1.5 g/ml of urethane. Anesthesia was verified by observing the reflex action of the leg. After verification of complete anesthesia, blood was collected through an insulin syringe. The blood thus obtained was immediately centrifuged at 2,500 rpm for 30 minutes at 4° C. to separate the serum.

4-1: Fat Accumulation and Liver Weight Reduction

After blood collection was completed, the mice were dissected, and the tissue was separated therefrom and was then quickly immersed in PBS to remove foreign substances from the surface. The weight and length of each tissue was measured, and then the tissue was fixed in a 10% formaldehyde solution and stored at −80° C. for subsequent analysis.

Figure 4:
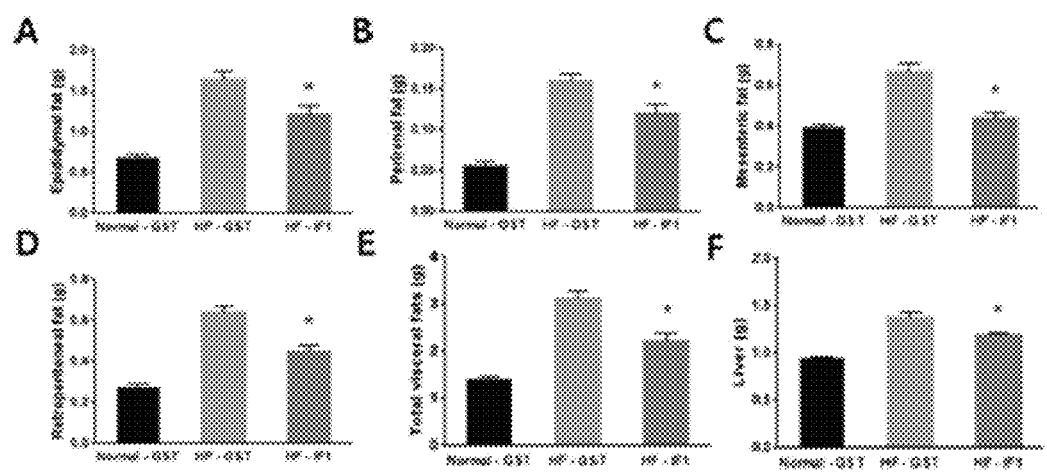
FIG. 4 shows the reduction in fat weight and liver weight in mouse tissue due to treatment with IF1, wherein (A) represents epididymal fat, (B) represents perirenal fat, (C) represents mesenteric fat, (D) represents retroperitoneal fat, (E) represents total visceral fat, and (F) represents liver weight, and *P<0.05 is satisfied upon comparison with an HF-GST group.

The weights of epididymal fat (FIG. 4A), perirenal fat (FIG. 4B), mesenteric fat (FIG. 4C), retroperitoneal fat (FIG. 4D) and total visceral fat (FIG. 4E) isolated from dissected mice were compared between the three mouse groups, and the liver weight (FIG. 4F) was also compared therebetween.

As a result, compared to the high-fat diet group, the fat mass in each tissue and total visceral fat mass of the IF1-administered group were significantly decreased, and the liver weight was also decreased.

4-2: Increased Muscle Mass

After blood collection was completed, the mice were dissected, and the muscles were separated therefrom and then quickly immersed in PBS to remove foreign substances from the surface. The weight of each of the quadriceps and the gastrocnemius was measured.

Figure 5:
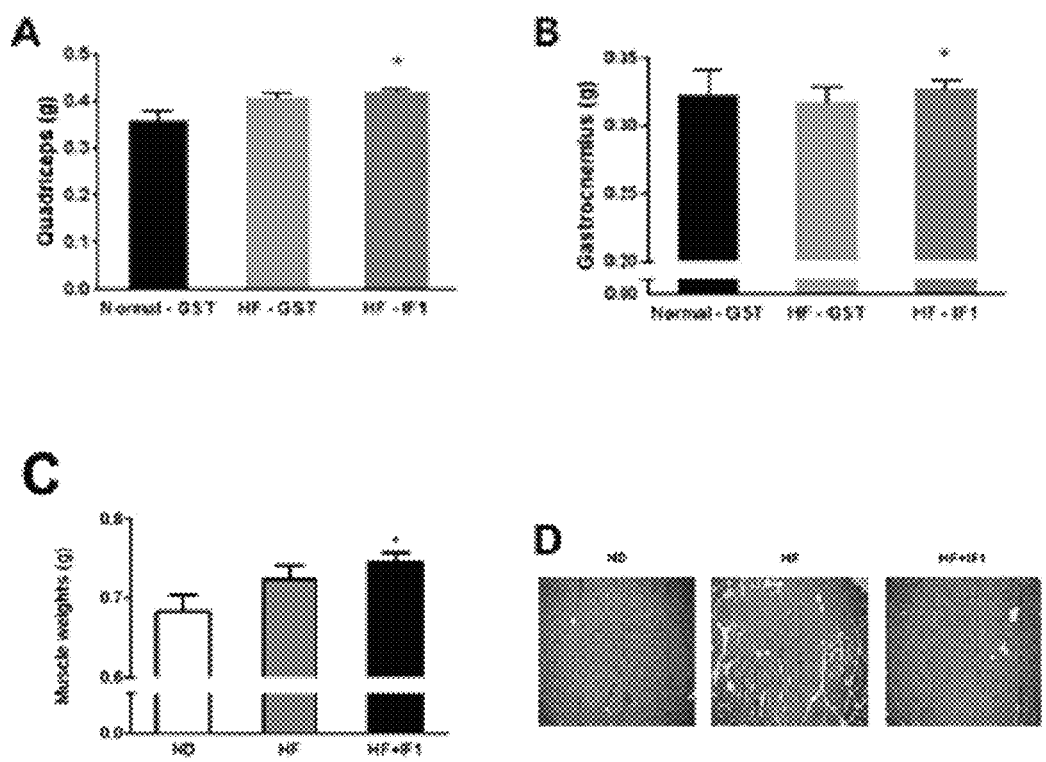
FIG. 5 shows the increase in muscle mass and muscle fiber density in mice due to treatment with IF1, wherein (A) represents quadriceps, (B) represents gastrocnemius, (C) represents the sum of the quadriceps and gastrocnemius weight, (D) represents the result of tissue immunostaining on the quadriceps, and each data point represents the mean±SE for each group, and *P<0.05 is satisfied upon comparison with an HF-GST group.

The result showed that the weight of quadriceps and gastrocnemius significantly increased in the IF1-administered group compared to the normal-diet and high-fat-diet control groups (FIGS. 5A to 5C). This means that IF1 is effective in increasing muscle mass.

In addition, in order to observe the changes in muscle cells, quadriceps and gastrocnemius, as muscle samples, were subjected to immunostaining (immunohistochemistry) using hematoxylin and eosin solutions. As a result, the muscle fiber density of the muscle tissue of the high-fat-diet group mice administered with IF1 was similar to that of the normal-diet group mice (FIG. 5D).

Example 5: Changes in Cells Constituting Adipose Tissue Due to IF1 Administration The change in the morphology of cells constituting the epididymal fat isolated from the mice of Example 4-1 was observed.

Figure 6:
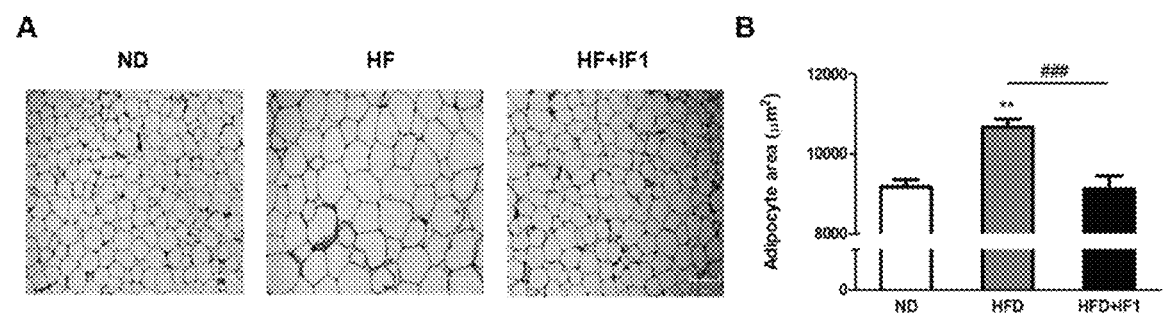
FIG. 6 shows changes in components in the mouse adipose tissue due to treatment with IF1, and shows the result of tissue immunostaining of epididymal fat and the average area of adipocytes and *P<0.05 and **P<0.01 are satisfied upon comparison with the ND group.

As a result, in the case of adipose tissue, the size of the adipocytes of the high-fat-diet control group increased significantly, whereas the IF1-administered group did not exhibit a significant difference from the normal diet control group (FIG. 6).

Example 6: Increased Muscle Protein Due to IF1 Administration

The total cellular protein of the quadriceps and gastrocnemius isolated in Example 4-2 was measured.

Specifically, 0.05 g of gastrocnemius tissue was lysed in RIPA lysis buffer containing a protease inhibitor and centrifuged at 4° C. and 13,000 rpm for 20 minutes, and the protein from the resulting supernatant was quantified through BCA assay.

Figure 7:
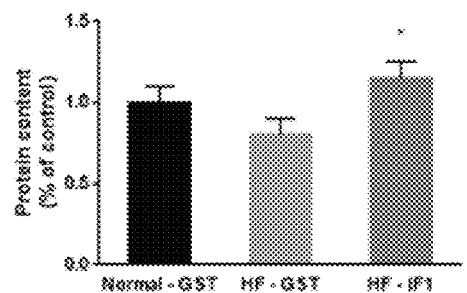
FIG. 7 shows an increase in the amount of gastrocnemius muscle protein in mice due to treatment with IF1, indicating that the amount of gastrocnemius muscle protein, which is decreased in obese mice, was increased by IF1 administration, wherein each data point represents the mean (relative to control, %) ±SE for each group and *P<0.05 is satisfied upon comparison with an HF-GST group.

The result showed that the mice induced with obesity using a high-fat diet exhibited a decreased amount of gastrocnemius protein, but the amount of gastrocnemius protein was significantly increased by IF1 administration (FIG. 7). That is, this shows that IF1 is effective in increasing muscle protein.

Example 7: Changes in Muscle-Related Gene Expression Due to IF1 Administration The expression levels of genes involved in muscle production and degradation in the quadriceps and gastrocnemius isolated in Example 4-2 were compared through qPCR (quantitative polymerase chain reaction) analysis.

Specifically, RNA was extracted from gastrocnemius tissue using a QIAzol Lysis Reagent RNeasy Lipid Tissue Mini Kit (Qiagen, USA), and cDNA was synthesized using 1 ug of RNA and oligo-dT (oligo-dT) and superscript II reverse transcriptase (Invitrogen, USA). Gene expression of 1,000 ng of the synthesized cDNA was compared through quantitative real-time PCR amplification. Data were obtained using the comparative-cycle threshold method and were expressed in fold change, and beta-actin was used as a control in a comparative CT method.

Figure 8:
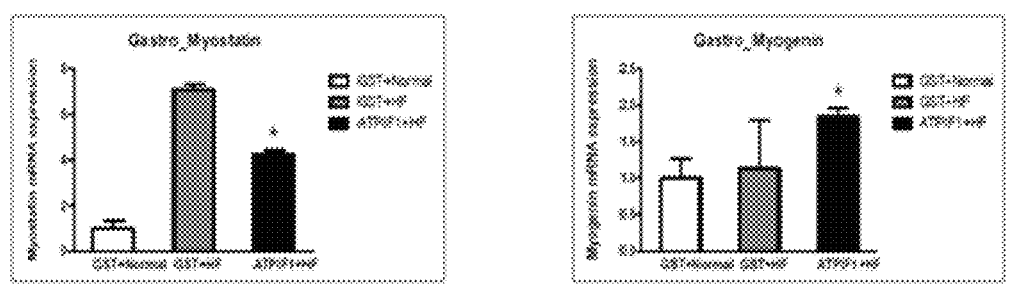
FIG. 8 shows the change in the expression of muscle-related genes in mice due to treatment with IF1, indicating a reduction in the expression of the myostatin gene, known as a negative regulator for muscle growth, and an increase in the expression of myogenin, which is a gene involved in muscle production, wherein each data point represents the mean (relative to control, %) ±SE for each group and *P<0.05 is satisfied upon comparison with an HF-GST group.

The result showed that the expression level of the myostatin gene, which is known to inhibit muscle production, was significantly reduced in the IF1-administered group compared to the high-fat diet control group. In addition, the result showed that the expression level of the myogenin gene, which is known to be involved in myogenesis, and the expression levels of IGF-1 and MYF5 genes were also increased (FIG. 8). That is, these results suggest that the extracellular ATP creates purine-like signaling, which leads to an increase in protein synthesis and inhibition of protein degradation by the subsequently triggered cellular signaling system.

Example 8: Activation of Nervous System Due to IF1 Administration and Regulation of Diet and Energy Metabolism Based Thereon In order to specifically determine whether or not the administration of IF1 can alleviate obesity-related diseases through diet control based on appetite suppression, enzyme-linked immunosorbent assay (ELISA) was performed on related hormones using the serum separated in Example 4. Changes in blood concentrations of norepinephrine (NE), which is known to suppress the appetite through activation of the central nervous system, as a major neurotransmitter of the sympathetic nervous system were detected.

Figure 9:
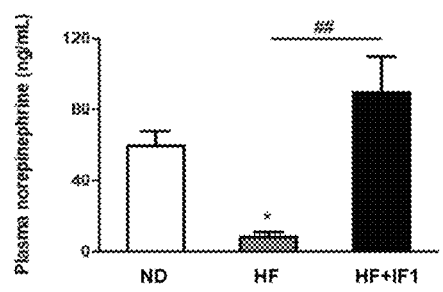
FIG. 9 shows the changes in the concentration of hormone in mouse blood and energy metabolism regulation index due to treatment with IF1, wherein (A) represents the concentration of norepinephrine in blood, (B) represents the mRNA expression of UCP-1 in subcutaneous tissue and the result of tissue immunostaining, and *P<0.05, P<0.01 and *P<0.001 are satisfied upon comparison with the ND group.
Figure 9:
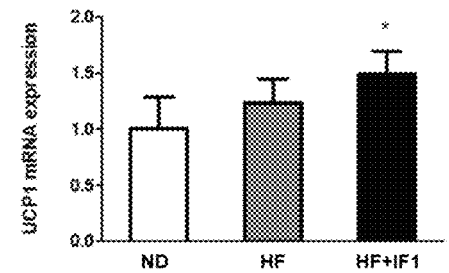
Figure 9:
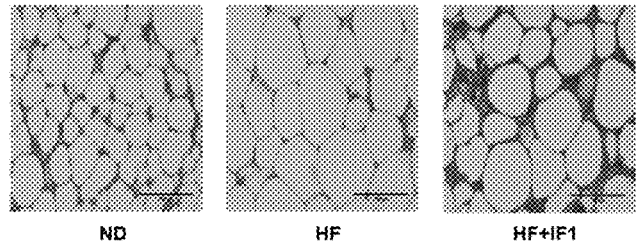

As a result, the high-fat-diet control group exhibited significantly decreased norepinephrine (NE) concentration, whereas the IF1-administered experimental group exhibited increased norepinephrine concentration compared to the normal diet control group (FIG. 9A).

Next, in order to determine whether or not stimulation of norepinephrine to the sympathetic nerve is associated with energy metabolism regulation, the expression level of UCP-1 (uncoupling protein 1), which regulates energy metabolism by conversion of white fat to brown fat, was observed.

As a result, an increase in expression of UCP-1 in subcutaneous fat tissue due to the administration of IF1 was confirmed by PCR and tissue immunostaining (FIG. 9B).

Example 9: Increased Muscle Strength of Animals Due to IF1 Administration

The muscle strength of obese model mice and aged model mice was measured to determine recovery and reinforcement of muscle function.

The obese model mice used herein were the mice of Example 1, the aged model animals used herein were average 8-month-old C57BL/6J female mice, and the normal diet and diets supplemented with GST and IF1 (5 mg/kg BW, once a week) were administered thereto while the mice aged for 2 months. The animals were rested for a period of 4 months, were randomly classified into the following two groups, and were treated with each of GST and IF1 (5 mg/kg BW, once daily) along with a high-fat diet. The breeding environment including a humidity of 50 to 60% at 18 to 24° C. was constantly maintained.

Group 1: High-fat diet (HFD) control+GST intraperitoneal injection (n=4)

Group 2: High-fat diet (HFD) experimental group+IF1 intraperitoneal injection (n=4) (5 mg/kg BW)

Figure 10:
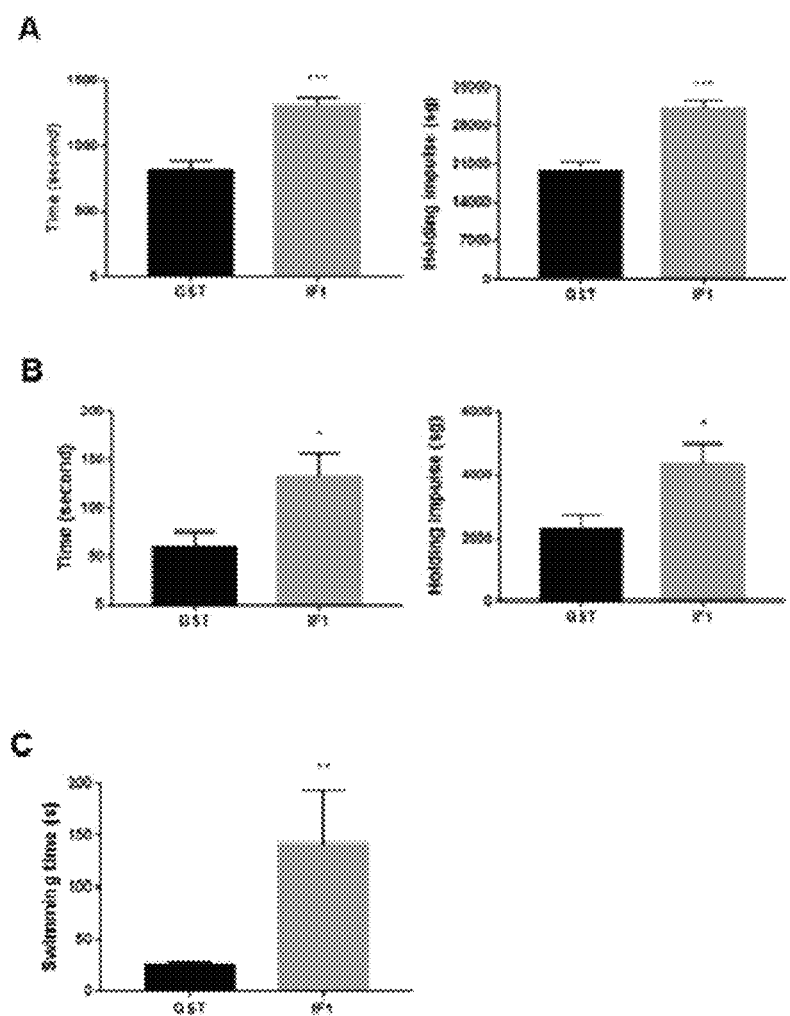
FIG. 10 shows the improvement and recovery of muscular functions in mice due to treatment with IF1, and includes hanging time and impulse calibrated therefrom using weight in (A) an obesity model and (B) an aged model during the hanging test, and (C) the swimming time (log 2) of the obese model mice through the improved FST (forced swimming test), wherein each data point represents the mean (relative to control, %) ±SE for each group, and *P<0.05, P<0.01 and *P<0.001 are satisfied upon comparison with the HF-GST group.

Muscle strength was measured using a hanging test (FIGS. 10A and 10B) and an improved FST (forced swimming test) (FIGS. 10C and 10D).

The hanging test was performed by measuring the time until a mouse hanging upside down from a 1×1 cm iron mesh grid fell to the floor, and the impulse is an index calibrated by multiplication of the weight. Both the obesity model (FIG. 10A) and the aged model (FIG. 10B) exhibited a significant increase compared to the control group, and this behavior was the same both before and after weight correction.

In the FST (forced swimming test), the obese model mice were familiarized with a water temperature of 34° C. and a flow rate of 2 L/min to allow each subject to become accustomed to the experimental environment, and the test was then performed at a different flow rate of 5 L/min. Only one mouse was tested in each lane, and the test was stopped when the mouse did not emerge from the water for a period of more than 7 seconds. The log-2 value obtained by treatment with IF1 exhibited a significantly increased swimming time compared to the control group (FIG. 10C). This has the same meaning as the hanging test of FIGS. 10A and 10B, indicating an increase in muscle strength in the IF1-treated group.

INDUSTRIAL APPLICABILITY

The IF1 (ATPase inhibitory factor 1) according to the present invention has effects of suppressing weight gain and lowering dietary intake without causing side effects in an obesity-induced mouse model, and has effects of increasing muscle mass and muscle protein mass and of inducing myogenesis without causing side effects in obesity-induced and aged mouse models, thus being very useful as an agent for preventing, ameliorating or treating metabolic diseases such as obesity, as an appetite suppressant, and as an agent for preventing, ameliorating or treating muscle-loss-related diseases such as sarcopenia.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

[Sequence Listing Free Text]

An electronic file is attached.

The invention claimed is:

1. A method for alleviating or treating obesity comprising administering recombinant exogenous ATPase inhibitory factor 1 (IF1) as an active ingredient to a subject in need thereof,
wherein the recombinant exogenous IF1 consists of the amino acid sequence of SEQ ID NO: 1.

2. The method according to claim 1, wherein said IF1 is administered with a pharmaceutically acceptable carrier, excipient or diluent.

3. A method for suppressing appetite comprising administering recombinant exogenous ATPase inhibitory factor 1 (IF1) as an active ingredient to a subject in need thereof,
wherein the recombinant exogenous IF1 consists of the amino acid sequence of SEQ ID NO: 1.

4. The method according to claim 3, wherein said IF1 is administered with a pharmaceutically acceptable carrier, excipient or diluent.

5. A method for treating sarcopenia comprising administering recombinant exogenous ATPase inhibitory factor 1 (IF1) as an active ingredient to a subject in need thereof,
wherein the recombinant exogenous IF1 consists of the amino acid sequence of SEQ ID NO: 1.

6. The method according to claim 5, wherein said IF1 increases muscle mass or prevents muscle loss.

7. The method according to claim 5, wherein the sarcopenia is caused by aging or obesity.

8. The method according to claim 5, wherein the sarcopenia is caused by muscular atrophy, disuse atrophy, spinal muscular amyotrophy, muscular dystrophy, spasticity, muscular hypotonia, muscle weakness, muscular dystrophy, amyotrophic lateral sclerosis, spinobulbar muscular atrophy, and myasthenia gravis.

9. The method according to claim 5, wherein said IF1 is administered with a pharmaceutically acceptable carrier, excipient or diluent.

* * * * *

SEQUENCE LISTING

```
<160> NUMBER OF SEQ ID NOS: 1

<210> SEQ ID NO 1
<211> LENGTH: 81
<212> TYPE: PRT
<213> ORGANISM: Artificial Sequence
<220> FEATURE:
<223> OTHER INFORMATION: Recombinant IF1

<400> SEQUENCE: 1

Val Ser Asp Ser Ser Asp Ser Met Asp Thr Gly Ala Gly Ser Ile Arg
1               5                   10                  15

Glu Ala Gly Gly Ala Phe Gly Lys Arg Glu Lys Ala Glu Glu Asp Arg
                20                  25                  30

Tyr Phe Arg Glu Lys Thr Lys Glu Gln Leu Ala Ala Leu Arg Lys His
            35                  40                  45

His Glu Asp Glu Ile Asp His His Ser Lys Glu Ile Glu Arg Leu Gln
        50                  55                  60

Lys Gln Ile Glu Arg His Lys Lys Lys Ile Gln Gln Leu Lys Asn Asn
65                  70                  75                  80

His
```